(12) United States Patent
Usher et al.

(10) Patent No.: US 10,517,972 B2
(45) Date of Patent: Dec. 31, 2019

(54) ANTI-BIOFOULING OF SUBMERGED LIGHTING FIXTURES

(71) Applicants: Scott D. Usher, Teaneck, NJ (US); Daniel Deutsch, New York, NY (US)

(72) Inventors: Scott D. Usher, Teaneck, NJ (US); Daniel Deutsch, New York, NY (US)

(*) Notice: Subject to any disclaimer, the term of this patent is extended or adjusted under 35 U.S.C. 154(b) by 0 days.

(21) Appl. No.: 16/537,739

(22) Filed: Aug. 12, 2019

(65) Prior Publication Data

US 2019/0360685 A1 Nov. 28, 2019

Related U.S. Application Data

(63) Continuation-in-part of application No. 14/957,812, filed on Dec. 3, 2015.

(60) Provisional application No. 62/089,315, filed on Dec. 9, 2014.

(51) Int. Cl.
*A61L 2/08* (2006.01)

(52) U.S. Cl.
CPC ..................... *A61L 2/08* (2013.01)

(58) Field of Classification Search
CPC ........................................................ A61L 2/08
See application file for complete search history.

(56) References Cited

U.S. PATENT DOCUMENTS

| | | |
|---|---|---|
| 4,098,610 A | 7/1978 | Wexell |
| 5,308,505 A | 5/1994 | Titus et al. |
| 5,322,569 A | 6/1994 | Titus et al. |
| 5,655,483 A | 8/1997 | Lewis et al. |
| 5,853,676 A | 12/1998 | Morgan, Jr. |
| 5,910,507 A | 6/1999 | Fellers et al. |
| 5,929,453 A | 7/1999 | Andrews et al. |
| 6,299,338 B1 | 10/2001 | Levinson et al. |
| 6,828,576 B2 | 12/2004 | Spivak |
| 6,830,699 B2 | 12/2004 | Heidal et al. |
| 7,081,225 B1 | 7/2006 | Hollander |
| 7,213,934 B2 | 5/2007 | Zarian et al. |
| 7,291,852 B1 | 11/2007 | Matlack et al. |
| 7,357,525 B2 | 4/2008 | Doyle |
| 7,425,718 B1 | 9/2008 | Baley et al. |
| 8,445,864 B2 | 5/2013 | Thoren et al. |
| 8,525,130 B2 | 9/2013 | Kim et al. |
| 8,575,637 B2 | 11/2013 | Bae et al. |
| 2002/0074559 A1 | 6/2002 | Dowling et al. |
| 2007/0170347 A1 | 7/2007 | Fournier et al. |
| 2008/0152548 A1 | 6/2008 | Clark et al. |

(Continued)

FOREIGN PATENT DOCUMENTS

CN 201935074 8/2011

*Primary Examiner* — Donald R Spamer
(74) *Attorney, Agent, or Firm* — Arthur Jacob

(57) ABSTRACT

A lighting fixture and method resist bio-fouling of the outer surface of a window of the lighting fixture when submerged and exposed to biological organisms within a surrounding environment. Ultraviolet radiation is directed to the outer surface of the window from a source inserted within the window, enabling transmission of ultraviolet radiation to the outer surface of the window of an intensity limited to essentially that which is effective in rendering the outer surface immune to adherence of biological organisms to which the outer surface of the window is exposed when submerged, and thereby allowing light from a source behind the window to be projected effectively through the window and into the surrounding environment.

12 Claims, 8 Drawing Sheets

(56) References Cited

U.S. PATENT DOCUMENTS

| | | |
|---|---|---|
| 2008/0246485 A1 | 10/2008 | Hibbs et al. |
| 2008/0265179 A1 | 10/2008 | Havens et al. |
| 2009/0320316 A1 | 12/2009 | Zakai |
| 2010/0042389 A1 | 2/2010 | Farruggia et al. |
| 2010/0278771 A1 | 11/2010 | Lobe et al. |
| 2011/0001060 A1 | 1/2011 | Welker |
| 2011/0286883 A1 | 11/2011 | Hecht et al. |
| 2012/0050520 A1 | 3/2012 | Thoren et al. |
| 2013/0048877 A1 | 2/2013 | Thoren et al. |
| 2014/0078584 A1 | 3/2014 | Farr et al. |
| 2014/0161663 A1 | 6/2014 | Farren et al. |
| 2014/0196745 A1 | 7/2014 | Whelan et al. |

ANTI-BIOFOULING OF SUBMERGED LIGHTING FIXTURES

This application is a continuation-in-part of U.S. patent application Ser. No. 14/957,812, filed Dec. 3, 2015, the entire disclosure of which is incorporated herein by reference thereto, which application claims the benefit of U.S. Provisional Patent Application Ser. No. 62/089,315, filed Dec. 9, 2014, the subject matter of which is incorporated herein by reference thereto.

The present invention relates generally to lighting fixtures constructed for installation where the lighting fixtures will be submerged and thereby exposed to biological organisms that can become attached in such manner as to interfere with the transmission of visible light from the lighting fixtures, and pertains, more specifically, to anti-biofouling constructions and methods for maintaining submerged lighting fixtures substantially free of such attachment of undesirable biological organisms.

With the advent of more effective, more efficient lighting apparatus, there has arisen a greater demand for lighting fixtures that can serve in submerged installations where these fixtures will be exposed to biological organisms that can become attached in a manner that will defeat the ability to serve the purpose of the installation. Thus, for example, lighting fixtures installed in marine environments, such as for the illumination of piers, pilings, seawalls and the like, as well as providing lighting for a variety of marine vessels, for illumination that is meant to serve either or both functional and decorative purposes, when placed at locations where the lighting fixtures will be submerged and thereby exposed to the attachment of biological organisms, such as barnacles, algae and the like, will soon lose effectiveness due to biofouling which will defeat the ability to transmit the desired illumination.

While it has been suggested that ultraviolet radiation (UV) can be effective in combating biofouling of optical surfaces of various equipment immersed for service in marine environments, the present invention provides specific constructions and methods for rendering lighting fixtures practical and effective in serving to illuminate a wide variety of installations where the lighting fixtures will be submerged and thereby exposed to the presence of biological organisms that can defeat the ability of the lighting fixtures to provide effective illumination for either functional or decorative purposes. Accordingly, the present invention attains several objects and advantages, some of which are summarized as follows: Provides constructions and methods for effectively combating biofouling of lighting fixtures installed to furnish lighting for either or both functional and decorative lighting purposes in environments where the lighting fixtures are submerged and thus exposed to biological organisms that can interfere with the proper transmission of light from the lighting fixtures; enables more widespread use of lighting fixtures for both functional and decorative lighting purposes where such lighting fixtures are submerged and exposed to the detrimental adherence of biological organisms and the concomitant impedance of the transmission of usable light as a result of biofouling; renders more economical the use of lighting fixtures in submerged environments, thereby opening the employment of submerged lighting fixtures over a wider and more diverse range of uses; simplifies the provision of practical anti-biofouling measures in lighting fixtures utilized in installations wherein the lighting fixtures are submerged and exposed to unwanted biological organisms; allows increased flexibility in the choice of design and construction of lighting fixtures to be submerged in environments where the lighting fixtures are exposed to potential biofouling; simplifies the installation of submerged anti-biofouling lighting fixtures in connection with a wide variety of marine structures, as well as marine vessels, without disturbing the integrity of such structures and vessels; exhibits a high degree of operating efficiency and effectiveness for more economical performance over an extended service life.

The above objects and advantages are attained by the present invention, which may be described briefly as a lighting fixture for providing illumination at a marine installation location, the lighting fixture being constructed for resisting bio-fouling when submerged in a surrounding marine environment and thereby exposed to visible light-impeding bio-fouling marine biological organisms within that environment, the lighting fixture comprising: a chamber sealed against the surrounding marine environment; a source of visible light within the chamber for providing illumination at the marine installation location; a window member located for transmitting illumination from the source of visible light into the surrounding marine environment, the window member having an outer surface through which outer surface the illumination is to pass upon placement of the outer surface in position to be exposed to the surrounding marine environment; and a source of ultraviolet radiation inserted within the window member and arranged to direct ultraviolet radiation comprised of UVC radiation for transmission to the outer surface of the window member, such that the UVC radiation at the outer surface of the window member is of an intensity limited to essentially that which is effective in rendering the outer surface of the window member immune to adherence of visible light-impeding bio-fouling marine biological organisms to which the outer surface of the window member will be exposed when submerged within the surrounding marine environment; the window member being constructed of a material capable of transmitting the UVC radiation from the source of ultraviolet radiation inserted within the window member, through the material of the window member, to the outer surface of the window member such that upon submersion of the lighting fixture within the surrounding marine environment, visible light-impeding bio-fouling marine biological organisms will be inhibited from adhering to the outer surface of the window member by UVC radiation emanating from the source of UVC radiation within the window member and transmitted through the material of the window member to the outer surface of the window member.

In addition, the present invention provides a method for resisting bio-fouling of a lighting fixture constructed to provide illumination at a marine installation location where the lighting fixture is submerged in a surrounding marine environment and thereby exposed to visible light-impeding bio-fouling marine biological organisms within that environment, the method comprising: providing the lighting fixture with a chamber sealed against the surrounding marine environment; placing a source of visible light within the chamber for providing illumination at the marine installation location; including a window member for transmitting illumination from the source of visible light into the surrounding marine environment, the window member having an outer surface through which outer surface the illumination will pass upon placement of the outer surface in position to be exposed to the surrounding marine environment; and combating adherence to the outer surface of the window member visible light-impeding bio-fouling marine biological organisms to which the outer surface of the window member will be exposed when submerged within the surrounding marine environment, by constructing the window member of a material capable of transmitting UVC radiation, inserting a source of UVC radiation within the window member and directing, from the source of UVC radiation within the window member for transmission through the material of the window member to the outer surface of the window member, UVC radiation of an intensity limited to essentially that which is effective in rendering the outer surface of the window member immune to adherence of such visible light-impeding bio-fouling marine biological organisms; whereby, upon submersion of the lighting fixture within the surrounding marine environment, visible light-impeding bio-fouling of the outer surface by adherence of light-impeding bio-fouling marine biological organisms will be inhibited by UVC radiation emanating from the source of UVC radiation inserted within the window member and passing through the material of the window member to the outer surface of the window member.

The invention will be understood more fully, while still further objects and advantages will become apparent, in the following detailed description of preferred embodiments of the invention illustrated in the accompanying drawing, in which.

Figure 1:
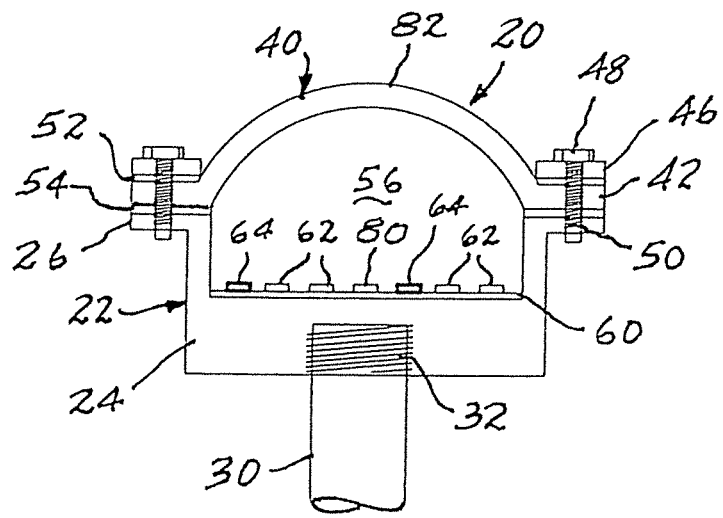
FIG. 1 is a partially diagrammatic, longitudinal cross-sectional view of a submersible lighting fixture constructed in accordance with the present invention.
Figure 2:
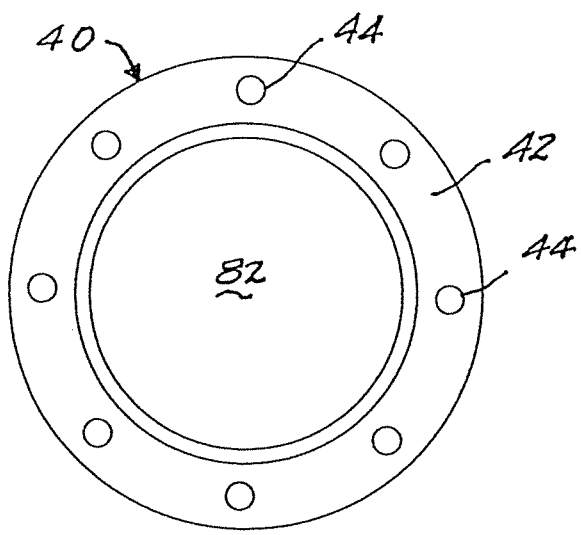
FIG. 2 is a plan view of a component part of the lighting fixture of FIG. 1.

Referring now to the drawing, and especially to FIGS. 1 and 2 thereof, a submersible lighting fixture constructed in accordance with the present invention is shown, partially diagrammatically, at 20 and is seen to include a housing 22 having a base 24 and a flange 26. Base 24 is shown mounted upon an underwater post 30 by means of a threaded connection at 32. A window member 40 includes a peripheral rim 42 having a plurality of holes 44 spaced apart circumferentially around the rim 42, and the window member 40 is secured to base 24 by a retaining ring 46 through which a plurality of threaded bolts 48 extend within holes 44 to be threaded into complementary threaded sockets 50 in flange 26 of housing 22. A first seal 52 is interposed between retaining ring 46 and rim 42 and a second seal 54 is interposed between rim 42 and flange 26, the first and second seals 52 and 54 serving to close and seal a chamber 56 within housing 22.

A circuit board 60 is placed within chamber 56, mounted upon base 24, and sealed against the environment outside lighting fixture 20 by virtue of placement within the sealed chamber 56. A source of illumination is provided by a plurality of light sources shown in the form of light emitting diodes (LEDs) 62 carried by circuit board 60 and operated by electronic circuitry 64 powered by an external power supply (not shown). LEDs 62 provide illumination which is directed through window member 40 to light the environment outside lighting fixture 20. In the illustrated embodiment, post 30 is mounted upon an underwater structure (not shown) and lighting fixture 20 is submerged, exposing lighting fixture 20, and especially window member 40, to biological organisms in the water within which lighting fixture 20 is submerged. These biological organisms, such as barnacles, algae and the like, will tend to adhere to window member 40 and obscure visible light being directed to the window member 40 by the LEDs 62 for transmission through the window member 40. This phenomenon is known as "biofouling" and will defeat the ability of a submerged lighting fixture to furnish the visible light desired at the installation.

It has been well established that ultra violet radiation is effective in countering the adherence of biological organisms to surfaces where it is desired to maintain these surfaces free of such biological organisms. In particular, ultra violet radiation identified as "UVC" radiation has been found effective in combating those biological organisms encountered in aquatic environments, and especially in marine environments. Accordingly, in order to maintain window member 40 immune to and substantially clear of any accumulation of biological organisms that could impede the transmission of illumination through window member 40, a source of UVC radiation is located within chamber 56, here shown in the form of a UVC LED 80 placed upon circuit board 60 and located so that UVC radiation is directed to window member 40. Window member 40 is constructed of a material, such as quartz, that is capable of transmitting UVC radiation, so that UVC radiation emanating from LED 80 will be transmitted through window member 40 to inhibit adhering of biological organisms upon the exterior surface 82 of window member 40 and thereby combat biofouling of window member 40. Energy is conserved by limiting the intensity of the transmitted UVC radiation at the external surface 82 to essentially that which is effective in rendering the external surface 82 immune to adherence of biological organisms. In the illustrated embodiment, window member 40 advantageously is constructed with exterior surface 82 having a domed configuration, and LED 80 is placed at a focal point of the domed configuration so that the intensity of UVC radiation is substantially uniform over the exterior surface 82. LED 80 is controlled by electronic circuitry 64 and, in the preferred arrangement, LED 80 need not be activated continuously, and is activated periodically, in timed, intermittent sessions, so as to conserve energy.

Housing 22 preferably is constructed, or at least coated, with a material that will resist biofouling, as well as corrosion, for long-term service. In addition, sealed chamber 56 preferably is evacuated, or is filled with an inert gas, such as nitrogen, to promote reliability and longevity of LEDs 62 and 80, as well as electronic circuitry 64.

Figure 3:
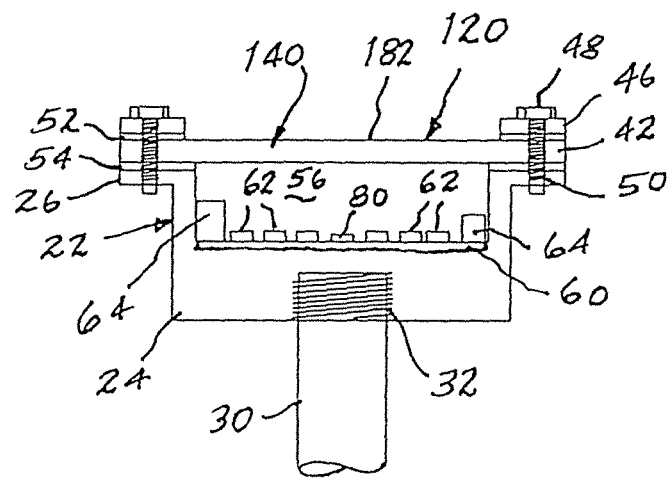
FIG. 3 is a partially diagrammatic, longitudinal cross-sectional view of another submersible lighting fixture constructed in accordance with the present invention.
Figure 4:
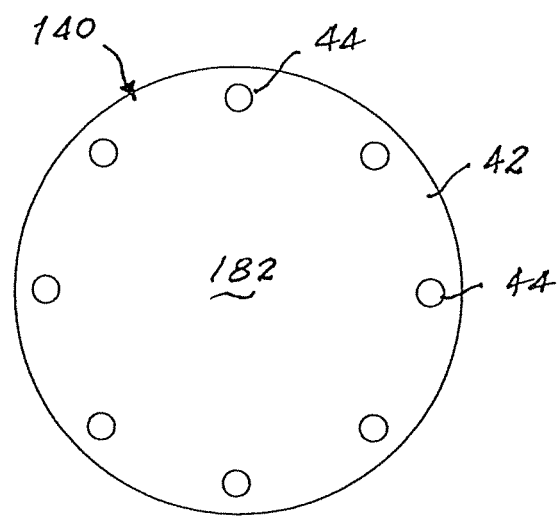
FIG. 4 is a top plan view of a component part of the lighting fixture of FIG. 3.

The embodiment illustrated in FIGS. 3 and 4 is shown in the form of a submersible lighting fixture 120 and is constructed similar to submersible lighting fixture 20 described in connection with FIGS. 1 and 2. Accordingly, corresponding component parts are labeled with the same reference characters and operate in the same manner as described above in connection with lighting fixture 20. However, in lighting fixture 120, window member 140 has a flat configuration, with a flat exterior surface 182, as opposed to the domed configuration of window member 40, the flat configuration providing both functional and decorative differences better suited to particular installations.

Figure 5:
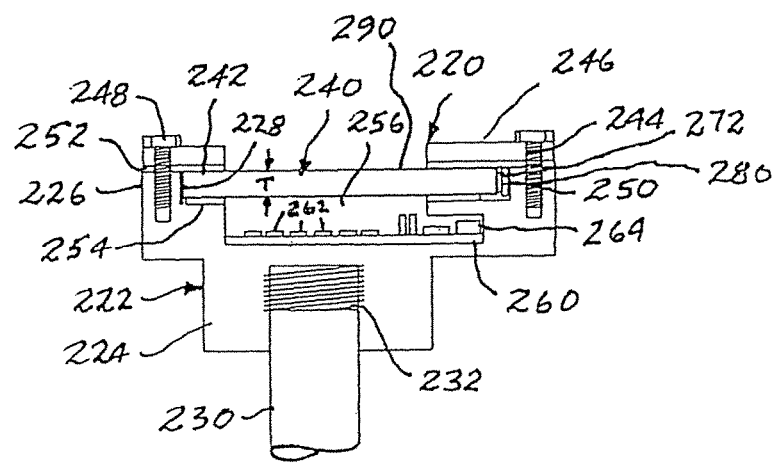
FIG. 5 is a partially diagrammatic, longitudinal cross-sectional view of still another submersible lighting fixture constructed in accordance with the present invention.
Figure 6:
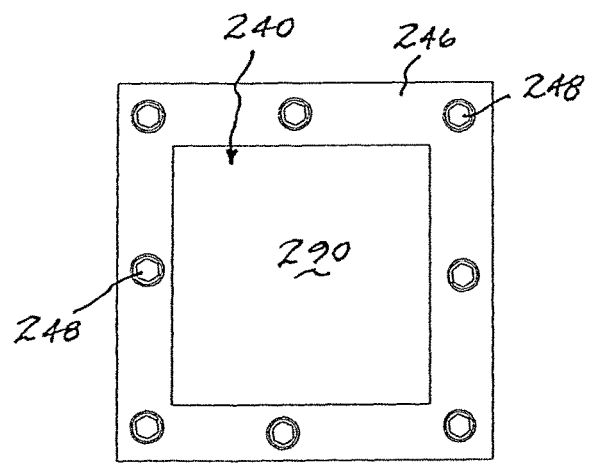
FIG. 6 is a top plan view of component parts of the lighting fixture of FIG. 5.
Figure 7:
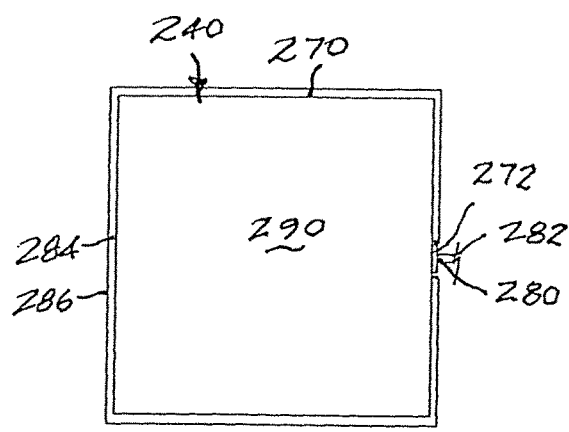
FIG. 7 is a top plan view of a component part of the lighting fixture of FIG. 5.

Turning now to FIGS. 5 through 7, another embodiment of the present invention is illustrated in the form of submersible lighting fixture 220 and is seen to have a housing 222 with a base 224, a flange 226 and a recess 228. Base 224 is shown mounted upon an underwater post 230 by means of a threaded connection at 232. A window member 240 includes a peripheral section 242, and is secured to base 224 by a retaining frame 246 juxtaposed with peripheral section 242 through which frame 246 a plurality of threaded bolts 248 extend within holes 244 to be threaded into complementary threaded sockets 250 in flange 226 of base 224. A first seal 252 is interposed between retaining frame 246 and peripheral section 242, and a second seal 254 is interposed between peripheral section 242 and base 224, the seals 252 and 254 serving to close and seal a chamber 256 within housing 222.

A circuit board 260 is placed within chamber 256, mounted upon base 224, and sealed against the environment outside lighting fixture 220 by virtue of placement within the sealed chamber 256. A plurality of light emitting diodes (LEDs) 262 are carried by circuit board 260 and are operated by electronic circuitry 264 powered by an external power supply (not shown). LEDs 262 provide illumination which is directed through window member 240 to light the environment outside lighting fixture 220.

Window member 240 has a predetermined thickness T, and a perimetric edge 270 that follows a largely rectangular path. A flat portion 272 is located along the perimetric edge 270 of window member 240, the flat portion 272 being adjacent flange 226 and spaced laterally a short distance from flange 226 to provide clearance for a source of UVC radiation, shown in the form of a UVC LED 280 coupled with window member 240 at the flat portion 272 along the perimetric edge 270 of window member 240. A lead 282 connects LED 280 to electronic circuitry 264 for operating LED 280. In the preferred construction, semi-rectangular portion 284 of perimetric edge 270 is coated with a UVC reflective material 286 such that upon activation of LED 280, UVC radiation is directed into window member 240 and, by virtue of internal reflection, normally is not dissipated out of window member 240 until such time as a biological organism comes into sufficient attachment to the outer surface 290 of window member 240, at which time UVC radiation within the window member 240 will be transmitted, by virtue of such attachment, to the interfering biological organism, resulting in the offending biological organism being neutralized so as to maintain the outer surface 290 sufficiently clear. In this manner, window member 240 functions similar to a waveguide, assisted by thickness T, providing UVC radiation only where, when and in an intensity limited essentially to that needed to maintain the outer surface 290 sufficiently clear of biofouling, thereby conserving energy.

Figure 8:
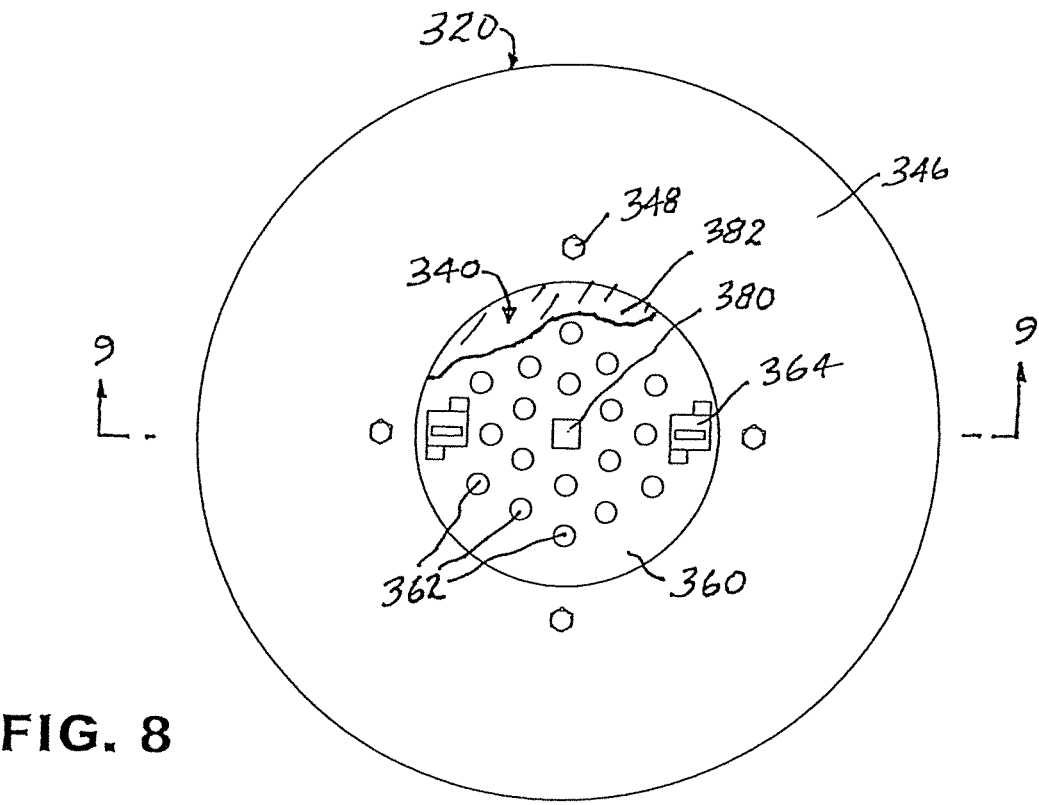
FIG. 8 is a top plan view of yet another submersible lighting fixture constructed in accordance with the present invention.
Figure 9:
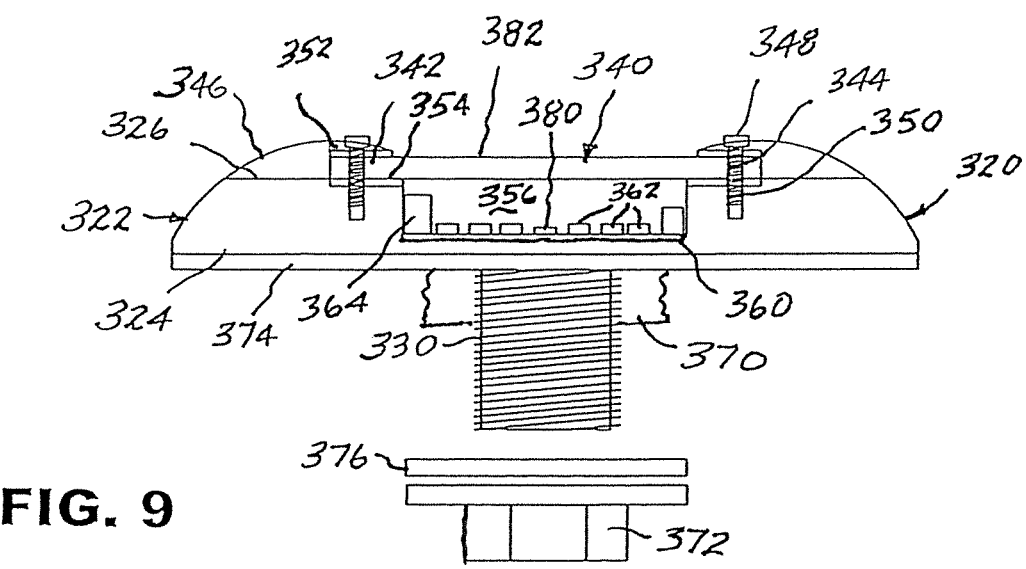
FIG. 9 is a partially diagrammatic cross-sectional view taken along line 9-9 of FIG. 8.

With reference to FIGS. 8 and 9, another submersible lighting fixture constructed in accordance with the present invention is shown, partially diagrammatically, at 320 and is seen to include a housing 322 having a base 324 and a flange 326. Base 324 carries a threaded post 330. A window member 340 includes a peripheral rim 342 having a plurality of holes 344 spaced apart circumferentially around the rim 342, and the window member 340 is secured to base 324 by a retaining ring 346 through which a plurality of threaded bolts 348 extend within holes 344 to be threaded into complementary threaded sockets 350 in flange 326 of base 324. A first seal 352 is interposed between retaining ring 346 and rim 342 and a second seal 354 is interposed between rim 342 and flange 326, the first and second seals 352 and 354 serving to close and seal a chamber 356 within housing 322.

A circuit board 360 is placed within chamber 356, mounted upon base 324, and sealed against the environment outside lighting fixture 320 by virtue of placement within the sealed chamber 356. A plurality of light emitting diodes (LEDs) 362 are carried by circuit board 360 and are operated by electronic circuitry 364 powered by an external power supply (not shown). LEDs 362 provide illumination which is directed through window member 340 to light the environment outside lighting fixture 320. In the illustrated embodiment, lighting fixture 320 is mounted upon an underwater structure, shown in the form of a hull 370 of a marine vessel, and is submerged, exposing lighting fixture 320, and especially window member 340, to biological organisms in the water within which lighting fixture 320 is submerged. Lighting fixture 320 is secured in place by advancing a threaded nut 372 along threaded post 330 until lighting fixture 320 is secured upon hull 370. A sealing member 374 is interposed between base 324 and hull 370, and a further sealing member 376 is interposed between threaded nut 372 and hull 370 to seal the hull 370. As described hereinbefore, biological organisms, such as barnacles, algae and the like, will tend to adhere to window member 340 and obscure visible light being directed to the window member 340 by the LEDs 362 for transmission through the window member 340. This phenomenon, known as "biofouling," will defeat the ability of a submerged lighting fixture to furnish the visible light desired at the installation.

Accordingly, in order to maintain window member 340 immune to and substantially clear of any accumulation of biological organisms that could impede the transmission of illumination through window member 340, a source of UVC radiation is located within chamber 356, here shown in the form of a UVC LED 380 placed upon circuit board 360 and located so that UVC radiation is directed to window member 340. Window member 340 is constructed of a material, such as quartz, that is capable of transmitting UVC radiation, so that UVC radiation emanating from LED 380 will be transmitted through window member 340 in an intensity limited essentially to that which is effective to inhibit adhering of biological organisms upon the exterior surface 382 of window member 340 and thereby combat biofouling of window member 340.

Figures 10, 11:
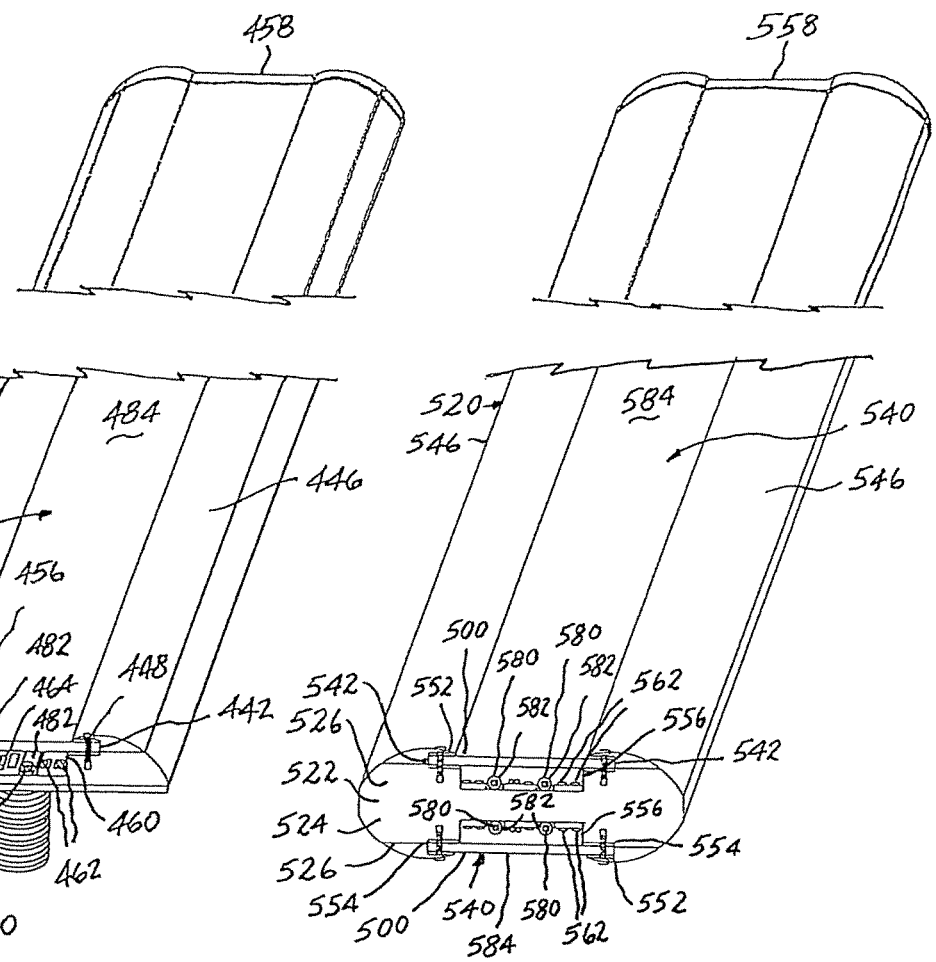
FIG. 10 is a partially diagrammatic cross-sectioned pictorial view of another submersible lighting fixture constructed in accordance with the present invention.
FIG. 11 is a partially diagrammatic cross-sectioned pictorial view of another submersible lighting fixture constructed in accordance with the present invention.

The embodiment of the invention illustrated in FIG. 10 is in the form of a submersible strip lighting fixture 420 having a housing 422 of a selected extended length, with a base 424 and a flange 426. Base 424 carries a number of threaded posts 430 along the length of the base 424 for mounting lighting fixture 420 upon a length of underwater structure. A window member 440 includes laterally opposite edges 442. The window member 440 is secured to base 424 by retaining members 446 through which a plurality of threaded bolts 448 extend to be threaded into flange 426 of base 424. A first seal 452 is interposed between each retaining member 446 and window member 440, and second seals 454 are interposed between window member 440 and base 424. The seals 452 and 454, together with opposite end caps, one of which end caps is shown at 458, serve to close and seal a chamber 456 within housing 422.

A circuit board 460 is placed within chamber 456, mounted upon base 424, and sealed against the environment outside lighting fixture 420 by virtue of placement within the sealed chamber 456. A plurality of light emitting diodes (LEDs) 462 are carried by circuit board 460 and are operated by electronic circuitry 464 powered by an external power supply (not shown). LEDs 462 provide illumination which is directed through window member 440 to light the environment outside lighting fixture 420.

In order to maintain window member 440 immune to and substantially clear of any accumulation of biological organisms that could impede the transmission of illumination through window member 440, sources of UVC radiation are located within chamber 456, here shown in the form of LEDs 480 placed within corresponding waveguides 482 carried by circuit board 460 and located so that UVC radiation of an effective limited intensity is directed to window member 440, distributed throughout the extended length of lighting fixture 420. Waveguides 482 and window member 440 are constructed of a material, such as quartz, that is capable of transmitting UVC radiation, so that UVC radiation emanating from LEDs 480 will be distributed to and pass through window member 440 to inhibit adverse accumulation of biological organisms upon the longitudinally extended exterior surface 484 of window member 440 and thereby combat biofouling of window member 440.

In the embodiment shown in FIG. 11, visible light emanates from both faces 500 of a submersible lighting fixture constructed in accordance with the present invention. Here again, a lighting fixture is in the form of strip lighting fixture 520 of selected, extended longitudinal length, having a housing 522 with a base 524. However, here base 524 includes opposite flanges 526. A window member 540 extends longitudinally along each face 500, and each window member 540 includes laterally opposite edges 542. Each window member 540 is secured to base 524 by retaining members 546 through which a plurality of threaded bolts 548 extend to be threaded into a corresponding flange 526 of base 524. Seals 552 and 554 are provided, as before, together with opposite end caps, one of which end caps is shown at 558, to close and seal chambers 556 within housing 522.

A plurality of light emitting diodes (LEDs) 562 are placed within each chamber 556, sealed against the environment outside lighting fixture 520 by virtue of placement within a corresponding sealed chamber 556, and are operated by corresponding electronic circuitry powered by an external power supply (not shown). LEDs 562 provide illumination which is directed through window members 540 to light the environment outside lighting fixture 520.

In order to maintain window members 540 immune to and substantially clear of any accumulation of biological organisms that could impede the transmission of illumination through window members 540, sources of UVC radiation are located within each chamber 556, here shown in the form of LEDs 580 placed within corresponding waveguides 582 located along the extended length of lighting fixture 520 so that UVC radiation is directed to window members 540, distributed throughout the extended length. Waveguides 582 and window members 540 are constructed of a material, such as quartz, that is capable of transmitting UVC radiation, so that UVC radiation emanating from LEDs 580 will be distributed to and pass through window members 540 to inhibit adverse accumulation of biological organisms upon the exterior surfaces 584 of window members 540 and thereby combat biofouling of window members 540.

Figure 12:
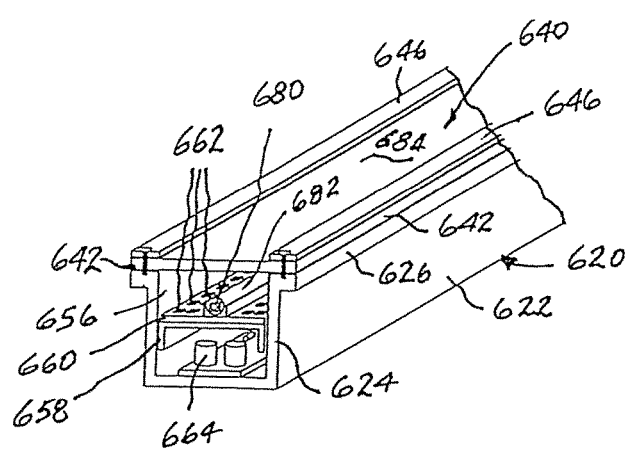
FIG. 12 is a partially diagrammatic cross-sectioned pictorial view of another submersible lighting fixture constructed in accordance with the present invention.

Turning now to FIG. 12, another submersible lighting fixture constructed in accordance with the present invention is shown in the form of an elongate lighting fixture 620 of selected, extended longitudinal length, having a housing 622 with a base 624 and a flange 626. A window member 640 includes laterally opposite edges 642 and is secured to base 624 by retaining members 646 which, together with end caps (not shown), establish a sealed chamber 656 in a manner similar to that described above.

A circuit board 660 is placed within chamber 656, mounted upon a bracket 658 affixed to housing 622, and sealed against the environment outside lighting fixture 620 by virtue of placement within the sealed chamber 656. A plurality of light emitting diodes (LEDs) 662 are carried by circuit board 660 and are operated by electronic circuitry 664 placed within sealed chamber 656 and powered by an external power supply (not shown). LEDs 662 provide illumination which is directed through window member 640 to light the environment outside lighting fixture 620.

In order to maintain window member 640 immune to and substantially clear of any accumulation of biological organisms that could impede the transmission of illumination through window member 640, sources of UVC radiation are located within chamber 656, here shown in the form of LEDs 680 placed within a waveguide 682 carried by circuit board 660 and located so that UVC radiation is directed to window member 640, distributed throughout the extended length of lighting fixture 620. Waveguide 682 and window member 640 are constructed of a material, such as quartz, that is capable of transmitting UVC radiation, so that UVC radiation emanating from LEDs 680 will be distributed to and pass through window member 640 to inhibit adverse accumulation of biological organisms upon the exterior surface 684 of window member 640 and thereby combat biofouling of window member 640.

Figure 13:
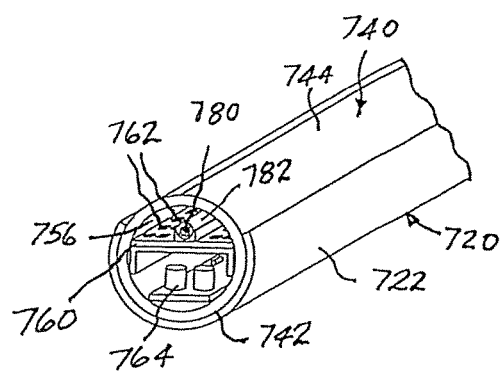
FIG. 13 is a partially diagrammatic cross-sectioned pictorial view of another submersible lighting fixture constructed in accordance with the present invention.

In the embodiment of the invention illustrated in FIG. 13, another submersible lighting fixture constructed in accordance with the present invention is shown in the form of an elongate lighting fixture 720 of selected, extended longitudinal length, having a housing member 722 extending longitudinally along the selected length. Housing member 722 has a semi-tubular configuration including a C-shaped cross-sectional contour. A window member 740 is in the form of a tubular structure 742 having a circular cross-sectional configuration essentially complementary to the cross-sectional configuration of housing member 722 so that window member 740 is received and retained within housing member 722, along the length of lighting fixture 720, while providing a window 744. End caps (not shown) are secured to housing member 722 to establish a sealed chamber 756 in a manner similar to that described above.

A circuit board 760 is placed within chamber 756, mounted upon a bracket 758 secured within window member 740, and is sealed against the environment outside lighting fixture 720 by virtue of placement within the sealed chamber 756. A plurality of light emitting diodes (LEDs) 762 are carried by circuit board 760, along the extended length of lighting fixture 720, and are operated by electronic circuitry 764 placed within sealed chamber 756 and powered by an external power supply (not shown). LEDs 762 provide illumination which is directed through window 744 to light the environment outside lighting fixture 720.

In order to maintain window 744 immune to and substantially clear of any accumulation of biological organisms that could impede the transmission of illumination through window 744, sources of UVC radiation are located within chamber 756, here shown in the form of LEDs 780 placed within a waveguide 782 carried by circuit board 760 and located along the extended longitudinal length of lighting fixture 720 so that UVC radiation is directed to window 744, distributed along the extended longitudinal length. Waveguide 782 and window member 740 are constructed of a material, such as quartz, that is capable of transmitting UVC radiation, so that UVC radiation emanating from LEDs 780 will be distributed to and pass through window 744 to inhibit adverse accumulation of biological organisms upon the exterior surface 784 of window 744 and thereby combat biofouling of window 744.

Figure 14:
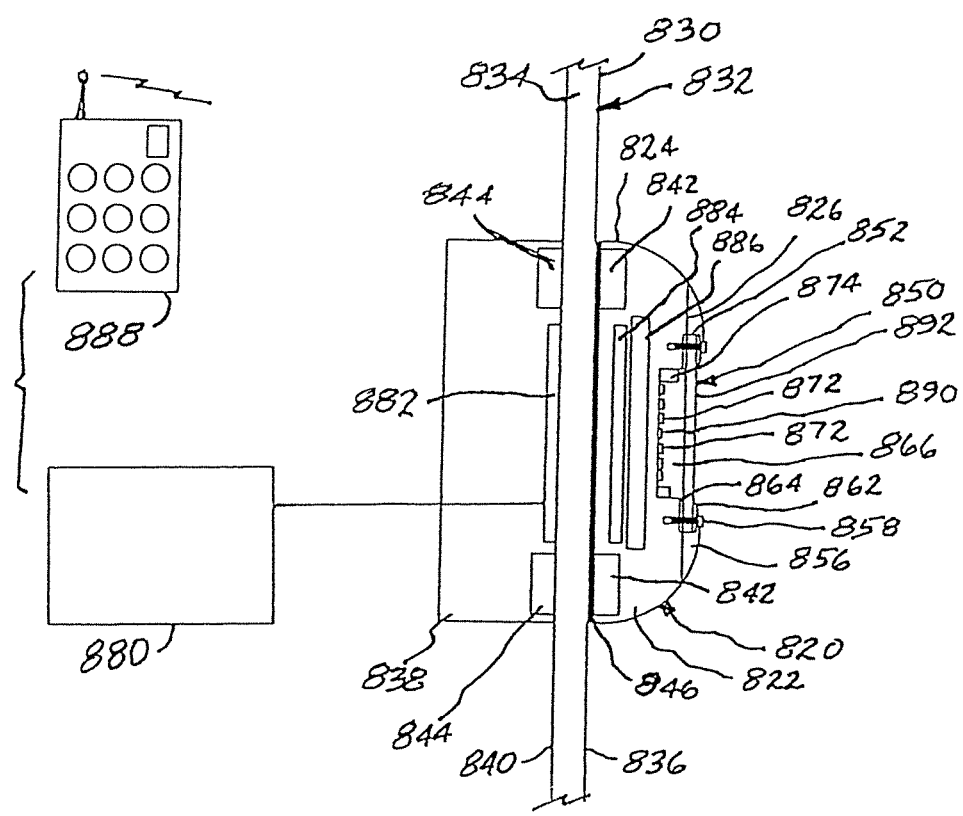
FIG. 14 is a partially diagrammatic cross-sectional view of a submersible lighting fixture constructed in accordance with the present invention and shown installed on a marine vessel.

With reference to FIG. 14, another submersible lighting fixture constructed in accordance with the present invention is shown, partially diagrammatically, at 820 and is seen to include a housing 822 having a base 824 and a flange 826. Lighting fixture 820 is shown mounted upon the hull 830 of a marine vessel 832 having a wall 834 constructed of a material now in common use in marine vessels, namely, a fiberglass reinforced synthetic polymeric material. The construction of lighting fixture 820 enables the lighting fixture 820 to be mounted upon hull 830 without compromising the integrity of wall 834. To that end, housing 822 is placed against outer face 836 of wall 834, in registration with an internal housing 838 placed against inner face 840 of wall 834, as shown. Housing 822 carries self-aligning rare earth magnets 842 affixed within housing 822 and which align with self-aligning rare earth magnets 844 carried by and affixed within internal housing 838. In this manner, corresponding magnets 842 and 844 are attracted to one another to secure in place housing 822, without the necessity for creating an unwanted opening or other compromising structural element in wall 834. Preferably, a resilient pad 846 is interposed between housing 822 and wall 834 to inhibit further any tendency toward unwanted movement of lighting fixture 820 along hull 830.

A window member 850 includes a peripheral rim 852 and is secured to base 824 by a retaining ring 856 through which a plurality of threaded bolts 858 extend to be threaded into flange 826 of base 824. First and second seals 862 and 864 close and seal a chamber 866 within housing 822.

A plurality of light emitting diodes (LEDs) 872 are placed within chamber 866, sealed against the environment outside lighting fixture 820 by virtue of placement within the sealed chamber 866 and are operated by electronic circuitry 874 powered by an external power supply 880. In order further to assure that wall 834 is maintained uncompromised, power supply 880 is coupled to a power induction transmitter 882 placed within internal housing 838, located within hull 830, and a power induction receiver 884 is placed within housing 822, in proximity to power induction transmitter 882. Power is transmitted to induction receiver 884 which is connected to an LED controller 886 which, in turn, is connected to electronic circuitry 874, all within housing 822. An RF transmitter/controller 888 within the vessel 832 communicates with LED controller 886 for enabling control of the LEDs 872, through electronic circuitry 874. In this manner, controlled power is furnished to LEDs 872 so as to provide desired illumination directed through window member 850 to light the environment outside lighting fixture 820. As described herein above, biological organisms, such as barnacles, algae and the like, will tend to adhere to window member 850 and obscure visible light being directed to the window member 850 by the LEDs 872 for transmission through the window member 850. This phenomenon, known as "biofouling," will defeat the ability of a submerged lighting fixture to furnish the visible light desired at the installation.

Accordingly, in order to maintain window member 850 immune to and substantially clear of any accumulation of biological organisms that could impede the transmission of illumination through window member 850, a source of UVC radiation is located within chamber 866, here shown in the form of a UVC LED 890 placed upon circuit board 870 and located so that UVC radiation is directed to window member 850. Window member 850 is constructed of a material, such as quartz, that is capable of transmitting UVC radiation, so that UVC radiation emanating from LED 890 will be transmitted through window member 850 to inhibit adverse accumulation of biological organisms upon the exterior surface 892 of window member 850 and thereby combat biofouling of window member 850.

Figure 15:
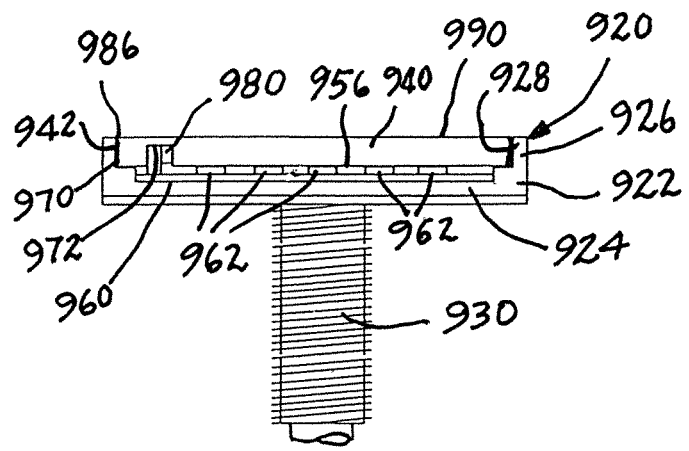
FIG. 15 is a partially diagrammatic, longitudinal cross-sectional view of another submersible lighting fixture constructed in accordance with the present invention.
Figure 16:
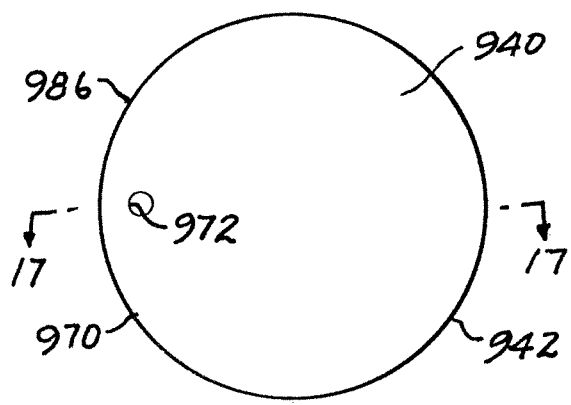
FIG. 16 is a bottom plan view of a component part of the lighting fixture of FIG. 15.
Figure 17:
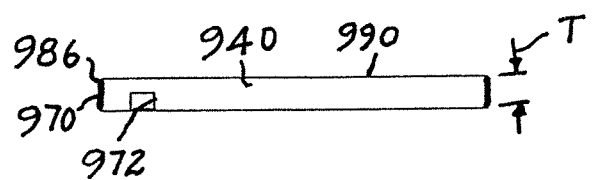
FIG. 17 is a cross-sectional view taken along line 17-17 of FIG. 16.

Turning now to FIGS. 15 through 17, another embodiment of the present invention is illustrated in the form of submersible lighting fixture 920 and is seen to have a housing 922 with a base 924, a flange 926 and a recess 928. A threaded post 930 extends from base 924 for mounting lighting fixture 920 in place at a selected installation site. A window member 940 includes a peripheral border 942, and is attached to base 924 by being securely fitted within flange 926 of base 924 to close and seal a chamber 956 within housing 922.

A circuit board 960 is placed within chamber 956, mounted upon base 924, and sealed against the environment outside lighting fixture 920 by virtue of placement within the sealed chamber 956. A plurality of light emitting diodes (LEDs) 962 are carried by circuit board 960 and are powered by an external power supply (not shown). LEDs 962 provide illumination which is directed through window member 940 to light the environment outside lighting fixture 920.

Window member 940 has a predetermined thickness T, and a perimetric edge 970 that preferably follows a largely circular path. A cavity 972 is located within window member 940, the cavity 972 preferably being adjacent perimetric edge 970 and spaced laterally a short distance from perimetric edge 970, cavity 972 being dimensioned and configured to accommodate a source of UVC radiation, shown in the form of a UVC LED 980 inserted within window member 940 adjacent the perimetric edge 970 of window member 940. LED 980 is coupled with circuit board 960 for operating LED 980. In the preferred construction, window member 940 is constructed of a material, such as quartz, that is capable of transmitting UVC radiation, so that UVC radiation emanating from LED 980 will be transmitted through window member 940. Perimetric edge 970 is provided with a coating 986 of UVC reflective material along the perimetric edge 970 such that upon activation of LED 980, UVC radiation is directed into window member 940 and, by virtue of internal reflection, normally is not dissipated out of window member 940 until such time as a biological organism comes into sufficient attachment to the outer surface 990 of window member 940, at which time UVC radiation within the window member 940 will be transmitted, by virtue of such attachment, to the interfering biological organism, resulting in the offending biological organism being neutralized and detached so as to maintain the outer surface 990 sufficiently clear. In this manner, window member 940 functions similar to a waveguide, assisted by thickness T, providing UVC radiation only where and when needed, essentially in an intensity limited to that which is effective to maintain the outer surface 990 sufficiently clear of biofouling, thereby conserving energy.

It will be seen that the present invention attains all of the objects and advantages summarized above, namely: Provides constructions and methods for effectively combating biofouling of lighting fixtures installed to furnish lighting for either or both functional and decorative lighting purposes in environments where the lighting fixtures are submerged and thus exposed to biological organisms that can interfere with the proper transmission of light from the lighting fixtures; enables more widespread use of lighting fixtures for both functional and decorative lighting purposes where such lighting fixtures are submerged and exposed to the detrimental adherence of biological organisms and the concomitant impedance of the transmission of usable light as a result of biofouling; renders more economical the use of lighting fixtures in submerged environments, thereby opening the employment of submerged lighting fixtures over a wider and more diverse range of uses; simplifies the provision of practical anti-biofouling measures in lighting fixtures utilized in installations wherein the lighting fixtures are submerged and exposed to unwanted biological organisms; allows increased flexibility in the choice of design and construction of lighting fixtures to be submerged in environments where the lighting fixtures are exposed to potential biofouling; simplifies the installation of submerged anti-biofouling lighting fixtures in connection with a wide variety of marine structures, as well as marine vessels, without disturbing the integrity of such structures and vessels; exhibits a high degree of operating efficiency and effectiveness for more economical performance over an extended service life.

It is to be understood that the above detailed description of preferred embodiments of the invention is provided by way of example only. Various details of design, construction and procedure may be modified without departing from the true spirit and scope of the invention, as set forth in the appended claims.

The embodiments of the invention in which an exclusive property or privilege is claimed are defined as follows:

1. A lighting fixture for providing illumination at a marine installation location, the lighting fixture being constructed for resisting bio-fouling when submerged in a surrounding marine environment and thereby exposed to visible light-impeding bio-fouling marine biological organisms within that environment, the lighting fixture comprising:
   a chamber sealed against the surrounding marine environment;
   a source of visible light within the chamber for providing illumination at the marine installation location;
   a window member located for transmitting illumination from the source of visible light into the surrounding marine environment, the window member having an outer surface through which outer surface the illumination is to pass upon placement of the outer surface in position to be exposed to the surrounding marine environment; and
   a source of ultraviolet radiation inserted within the window member and arranged to direct ultraviolet radiation comprised of UVC radiation for transmission to the outer surface of the window member, such that the UVC radiation at the outer surface of the window member is of an intensity limited to essentially that which is effective in rendering the outer surface of the window member immune to adherence of visible light-impeding bio-fouling marine biological organisms to which the outer surface of the window member will be exposed when submerged within the surrounding marine environment;
   the window member being constructed of a material capable of transmitting the UVC radiation from the source of ultraviolet radiation inserted within the window member, through the material of the window member, to the outer surface of the window member such that upon submersion of the lighting fixture within the surrounding marine environment, visible light-impeding bio-fouling marine biological organisms will be inhibited from adhering to the outer surface of the window member by UVC radiation emanating from the source of UVC radiation within the window member and transmitted through the material of the window member to the outer surface of the window member.

2. The lighting fixture of claim 1 wherein the material of the window member is quartz.

3. The lighting fixture of claim 1 wherein the source of visible light comprises at least one LED.

4. The lighting fixture of claim 1 wherein the window member includes a perimetric edge, and the source of ultraviolet radiation is located adjacent the perimetric edge.

5. The lighting fixture of claim 1 wherein the window member includes a perimetric edge, and a coating of UVC reflective material along the perimetric edge.

6. The lighting fixture of claim 5 wherein the source of ultraviolet radiation is located adjacent the perimetric edge.

7. A method for resisting bio-fouling of a lighting fixture constructed to provide illumination at a marine installation location where the lighting fixture is submerged in a surrounding marine environment and thereby exposed to visible light-impeding bio-fouling marine biological organisms within that environment, the method comprising:
   providing the lighting fixture with a chamber sealed against the surrounding marine environment;
   placing a source of visible light within the chamber for providing illumination at the marine installation location;
   including a window member for transmitting illumination from the source of visible light into the surrounding marine environment, the window member having an outer surface through which outer surface the illumination will pass upon placement of the outer surface in position to be exposed to the surrounding marine environment; and
   combating adherence to the outer surface of the window member visible light-impeding bio-fouling marine biological organisms to which the outer surface of the window member will be exposed when submerged within the surrounding marine environment, by constructing the window member of a material capable of transmitting UVC radiation, inserting a source of UVC radiation within the window member and directing, from the source of UVC radiation within the window member for transmission through the material of the window member to the outer surface of the window member, UVC radiation of an intensity limited to essentially that which is effective in rendering the outer surface of the window member immune to adherence of such visible light-impeding bio-fouling marine biological organisms;

whereby, upon submersion of the lighting fixture within the surrounding marine environment, visible light-impeding bio-fouling of the outer surface by adherence of light-impeding bio-fouling marine biological organisms will be inhibited by UVC radiation emanating from the source of UVC radiation inserted within the window member and passing through the material of the window member to the outer surface of the window member.

8. The method of claim 7 wherein the material of the window member is quartz.

9. The method of claim 7 wherein placing the source of visible light comprises placing at least one LED in the chamber.

10. The method of claim 7 including providing the window member with a perimetric edge, and locating the source of ultraviolet radiation adjacent the perimetric edge.

11. The method of claim 7 including providing the window member with a perimetric edge, and providing a coating of a UVC reflective material along the perimetric edge.

12. The method of claim 11 including locating the source of ultraviolet radiation adjacent the perimetric edge.

\* \* \* \* \*